United States Patent

Roy et al.

[11] Patent Number: 6,118,540
[45] Date of Patent: Sep. 12, 2000

[54] METHOD AND APPARATUS FOR INSPECTING A WORKPIECE

[75] Inventors: Rajiv Roy, Plano; Michael C. Zemek, Richardson; Weerakiat Wahawisan, Carrollton, all of Tex.

[73] Assignee: Semiconductor Technologies & Instruments, Inc., Plano, Tex.

[21] Appl. No.: 08/890,814

[22] Filed: Jul. 11, 1997

[51] Int. Cl.[7] .................................. G01B 11/00
[52] U.S. Cl. .............. 356/394; 356/237.5; 348/126; 29/759
[58] Field of Search .................... 356/394, 237, 356/398, 375, 376, 237.1, 237.4, 237.5; 348/187, 189, 87, 126

[56] References Cited

U.S. PATENT DOCUMENTS

| | | | |
|---|---|---|---|
| 3,671,726 | 6/1972 | Kerr | 235/151.3 |
| 4,199,253 | 4/1980 | Ross | 356/5 |
| 4,259,589 | 3/1981 | DiMatteo et al. | 250/556 |
| 4,733,969 | 3/1988 | Case et al. | 356/375 |
| 4,739,175 | 4/1988 | Tamura | 250/561 |
| 4,772,125 | 9/1988 | Yoshimura et al. | 356/237 |
| 4,774,403 | 9/1988 | Arts | 250/205 |
| 4,793,707 | 12/1988 | Hata et al. | 356/375 |
| 4,872,052 | 10/1989 | Liudzius et al. | 358/106 |
| 4,880,307 | 11/1989 | Endo et al. | 356/375 |
| 4,891,772 | 1/1990 | Case et al. | 364/562 |
| 4,900,146 | 2/1990 | Penney et al. | 356/1 |
| 4,978,220 | 12/1990 | Abramovich et al. | 356/394 |
| 4,980,971 | 1/1991 | Bartschat et al. | 29/833 |
| 5,024,529 | 6/1991 | Svetkoff et al. | 356/376 |
| 5,032,735 | 7/1991 | Kobayashi et al. | 356/394 |
| 5,058,178 | 10/1991 | Ray | 356/237 |
| 5,084,959 | 2/1992 | Ando et al. | 29/740 |
| 5,140,643 | 8/1992 | Izumi et al. | 382/8 |
| 5,166,533 | 11/1992 | Kajiwara | 250/561 |
| 5,379,106 | 1/1995 | Baldur | 356/375 |
| 5,686,994 | 11/1997 | Tokura | 356/394 |
| 5,694,219 | 12/1997 | Kim | 356/375 |

*Primary Examiner*—Hoa Q. Pham
*Attorney, Agent, or Firm*—Akin, Gump, Strauss, Hauer & Feld, LLP

[57] ABSTRACT

A computer vision apparatus and methods for automatically inspecting 2-dimensional (2D) and 3-dimensional (3D) criteria of objects using a single camera and laser sources. A camera views the object under inspection which is illuminated by a first source of light to highlight the region of interest. This provides image data for 2d analysis by a computer coupled to the system. Subsequently, multiple laser sources mounted on a positioner provide the illumination for collecting images for 3 dimensional analysis. A computer with a monitor is connected to the camera to perform the inspection and analysis and for operator supervision of the system. Specific implementations provided refer to embodiments for inspecting packaged semiconductor devices such as Ball-Grid Arrays (BGAs) packages and Quad Flat Packages (QFPs) packages for package mark inspection, package defect inspection, and solder ball or lead defects. Further, the apparatus and methods of the invention can be applied to the inspection of chip sized packages and to Flip-Chip Bump, and I.C. Die inspection. The system can also be used to inspect bond wire Wire Loop Height and to perform automated Quality Inspection for critical assembly of disk-drives, CD-Roms, keyboards, other assemblies in the computer industry and in other industries.

17 Claims, 7 Drawing Sheets

QFP 2D Inspection process

METHOD AND APPARATUS FOR INSPECTING A WORKPIECE

BACKGROUND OF THE INVENTION

1. Field of the Invention

The invention relates generally to the use of automatic inspection of objects to perform three dimensional and two dimensional criteria analysis, and more specifically to the use of two and three dimensional criteria analysis to perform lead inspection, package mark and package inspection of integrated circuit devices including semiconductor circuits. The techniques and methods of the invention can also be applied to the inspection of solder balls of Ball Grid Array (BGA) integrated circuit packages and to the inspection of Chip Sized Packages (CSP) integrated circuit packages using computer vision.

2. Description of Related Art

This invention relates to combining two dimensional and three dimensional automated imaging inspection in a system. In the prior art, there are several approaches and some commercial applications which perform two dimensional (2D) and three dimensional (3D) image inspections individually. There are known systems which perform lead inspection (looking for and sometimes correcting bent leads), package mark inspection (checking the vendors mark and device number and type designators which are typically painted or printed on the plastic body of the package) and package defect inspection (holes, cracks or other irregularities in the surface of the plastic packaged device) of semiconductor packages. There also several known approaches relating to semiconductor package lead inspection of quad flat packages (hereinafter referred to as QFPs) and ball grid array packages (BGAs).

The following U.S. Patents are referred to herein as references typifying the approaches of the prior art.

| | | |
|---|---|---|
| 2d Mark Inspection | 4,589,141 | 5/1986 Christian et al. |
| 3d Lead Inspection | 5,414,458 | 5/1995 Harris et al. |
| 3d Thickness Inspection | 3,671,726 | 6/1972 Kerr et al. |
| 3d Information | 4,259,589 | 3/1981 DiMatteo et al. |
| 3d Sensors | 4,891,772 | 1/1990 Case et al. |
| 3d LaserProbe | 4,733,969 | 3/1988 Case et al. |
| 3d Imaging | 5,024,529 | 6/1991 Svetkoff et al. |
| 3d Triangulation | 4,774,403 | 9/1988 Arts et al. |

Several commercially available systems for inspecting integrated circuit packages are available. View Engineering provides systems where the image of a single point laser that oscillates at a high frequency, visible as a line on the object, is input into a camera. The laser points straight down from above the device undergoing inspection with the camera looking at an angle. The camera and laser source form the laser head. This laser head has to move over the entire device to generate a complete 3d image of the object. There are several problems with this approach . An X-Y positioner with a travel of greater than about 6"×12" is required to move the laser head over a tray of devices. In addition, the X-Y positioner has to be attached to large granite blocks to dampen vibrations which could distort the results A separate camera performs a second inspection for package mark and package defects at a separate location on the machine.

In a system available from RVSI, Incorporated, a single point laser, with a one or more sensors, is used to triangulate to determine 3D inspection criteria. The laser sensors and the laser source form the laser head. This laser head is then moved over the device several times to generate 3D information of the points under the laser. The laser points straight down with the sensors at an angle to the laser.

Again, with the RVSI approach, an X-Y head positioner with a travel of greater than about 6"×12" is required to move the laser head over a tray of devices. In addition, the X-Y positioner again has to be attached to large granite blocks to dampen vibrations. Package mark inspection and package defect inspection is performed by a separate camera placed at a separate location on the machine. For quad flat packages (QFPs), the package has to be placed so as have to be "live bug" (package normal orientation). However, for ball grid array packages (BGAs), these devices have to be placed "dead-bug" (upside down) for the inspection.

In systems available from ICOS, Incorporated, four light sources are used to form a shadow of the device leads. A single camera looks upwards to analyze the displacement of the shadow to determine 3D displacement of leads and so perform lead inspection. No laser light source is used. Again, there are several problems in this approach. As with the other systems, a separate camera inspects for package mark and package defects. The system cannot inspect BGA packages.

In systems currently available from Texas Instruments Incorporated, a single camera is used to look at the silhouette of the leads. The device is rotated four times to generate 4 images which is then analyzed to determine 3d displacement of leads. No laser light source is used. With this system, QFPs have to be positioned upside down and the system cannot inspect BGAs. Also, as with the other systems, a separate camera inspects for package mark and package defects.

Further with respect to the existing systems, most systems using triangulation to perform 3D criteria inspection have laser light sources going straight down at the object with the camera positioned at an angle of about 45 degrees. This implies modifying the plane of the CCD imager of the camera in order to achieve the Schiempflug condition of the optical axis of the lens, with the plane of the CCD imager and the plane of the laser source intersecting at a point. It is important to achieve this condition to have optimal focus of the object being looked at. This aspect of the prior art systems requires modifying a camera based on a CCD system.

Accordingly, a need thus exists for an apparatus and method for performing computer vision analysis of objects using a single camera solution to perform two-dimensional and three dimensional criteria analysis.

SUMMARY OF THE INVENTION

The inspection system of the invention described herein uses fiber optics ring light or LED based ring-light as a light source to illuminate the 2D scenes, depending on the type of inspection required. There is a plurality of lasers mounted to motorized linear positioners that provides structured light based illumination for performing the 3D criteria measurements. In performing inspections of semiconductor devices and micro-electronics, the devices can be completely inspected using 4 lasers. Triangular -shaped objects could be inspected using three laser sources while larger polygonal shapes could deploy more lasers to provide appropriate coverage.

In the system of the invention, the 2D lighting is switched on first to illuminate the object. The single camera captures the image and presents it to a computer system for image analysis. On analysis of the scene, the system determines the absence or presence of defects that fall into the 2D category, and location of portions of the object that need 3D criteria analysis.

Once the X-Y location of the area needing 3D inspection is determined, the plurality of lasers are positioned over the area and then moved at a constant velocity while a plurality of images are collected by the camera. Analysis of the location of the laser stripe, given the location information provided by the encoder for the linear positioner of the laser, provides information as to the displacement, in 3 dimensions, for that area of the object.

The unique features of this invention are that it provides combined 2D inspection criteria, such as package mark inspection and package defect inspection, along with 3D inspection such as lead coplanarity, in a single camera system. This is in contrast to the existing systems which use either multiple cameras or laser triangulation to inspect for 3D inspection criteria and subsequently perform the 2D criteria at a separate camera.

In one embodiment of the invention, the camera is provided looking straight down or up at the object, so the object does not appear tilted and hence there is no need for the achieving focus through the Schiempflug condition. Hence use of the invention described herein results in a reduction in assembly costs in not having to modify cameras.

In contrast to the prior art systems, no granite or large X-Y positioner is required to move the laser head over the leads. While the laser head is stationary, positioned over the device, laser sources mounted onto small slides scan the leads. This approach advantageously does not require large mass for damping.

The system of the invention also provides the flexibility of being able to inspect the package in a variety of orientations. This feature of the system allows the device inspection head to adapt to the system on which the device is to be inspected rather than modifying the system to adapt to the inspection head. For example, QFP packages can be inspected live bug or dead-bug (normal or upside down orientation, respectively)—with the camera pointing down or up towards the device. BGAs can be inspected live bug (Camera pointing up) or dead-bug (camera pointing down). Package mark and package defects can be inspected on the same station when inspecting QFPs in the live bug orientation. Substrate defects can be inspected on the BGA packages at the same station as other package types.

These and other objects, advantages and features of this invention will be apparent from the following description taken with reference to the accompanying drawing, wherein is shown a preferred embodiment of the invention.

BRIEF DESCRIPTION OF THE DRAWING

Corresponding numerals and symbols in the different figures refer to corresponding parts unless otherwise indicated in the specification and the figures.

DESCRIPTION OF THE PREFERRED EMBODIMENT

Figure 1:
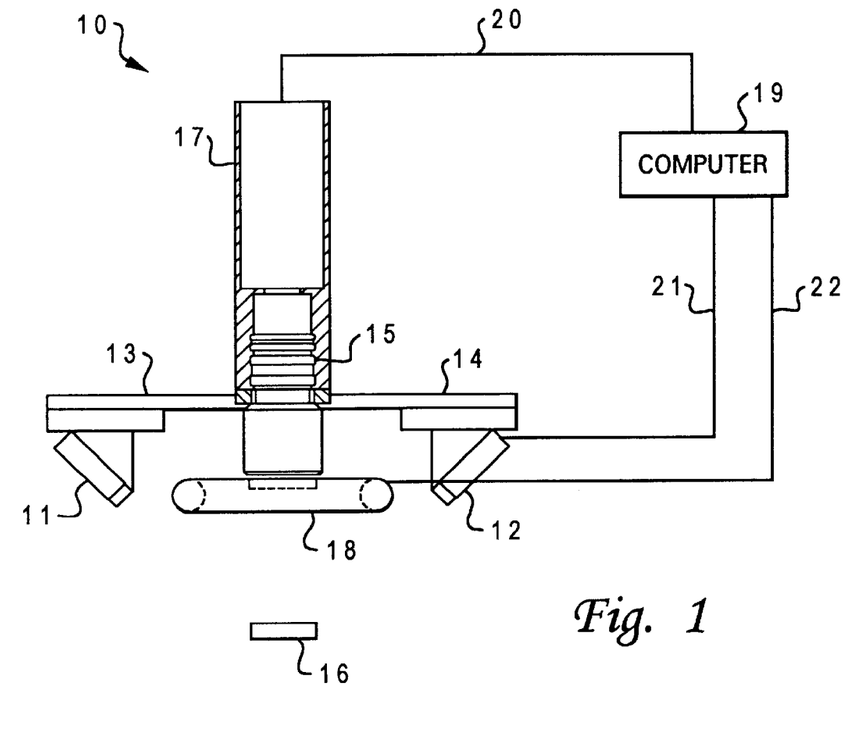
FIG. 1 is a pictorial representation of a first embodiment of the apparatus of the in invention.

Referring now to the drawing, and in particular to FIG. 1, a system according to the present invention is referred to generally by reference numeral 10 and a workpiece to be inspected is referred to by reference numeral 16. A laser source 11 is mounted to a linear positioner 13. Three (alternatively, more could be used) other lasers are mounted to other linear positioners placed 90 degrees apart. A laser source 12 mounted to a linear positioner 14 is another example of laser mounted to a positioner. This arrangement produces the source of light for the 3D image which is imaged through lens 15 and received by camera 17. Some light source such as a ring-light 18 may be used to produce a 2D image. This ring-light could change to other light sources depending on the nature of workpiece 16 being inspected. The image 25 from the camera is input into a personal computer (PC) class computer, 19, via cable 20. Other computers could be used, such as workstations, mainframes, or smaller computers such as industrial type microcontrollers or programmable personal digital assistants or notebooks, laptops, etc. The laser sources and the ring-light are switched on and off when needed by the PC via cables 21 and 22.

Figure 2:
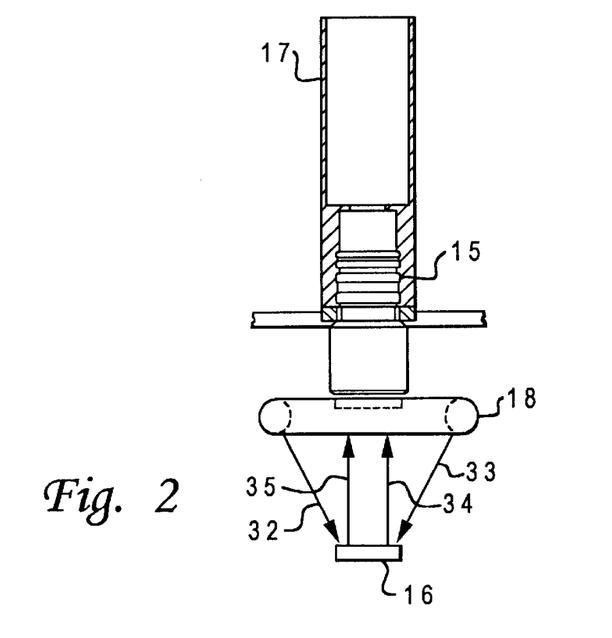
FIG. 2 is a view of the optical path used for 2D inspection in a preferred method of the invention of FIG. 1.
Figure 3:
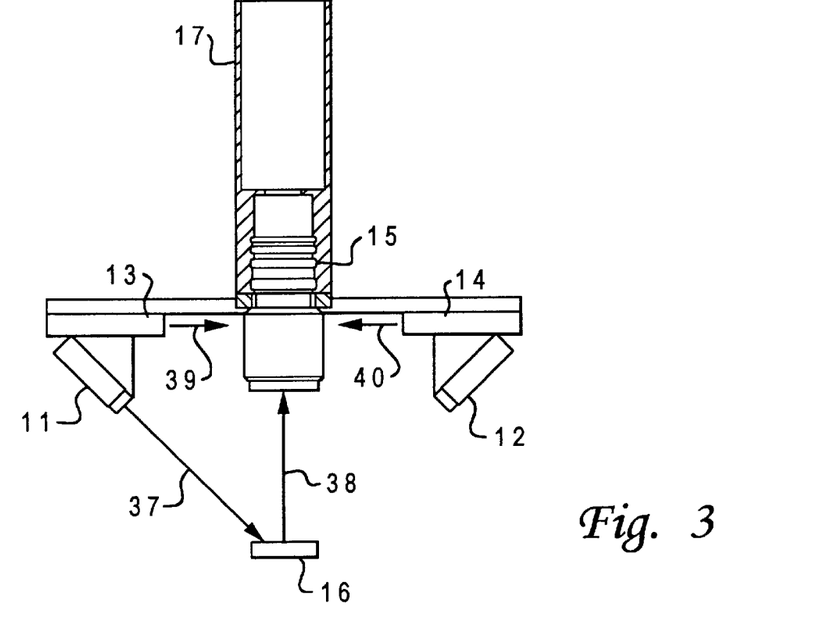
FIG. 3 is a view of the optical path used for 3D inspection in a preferred method of the invention of FIG. 1.
Figure 4:
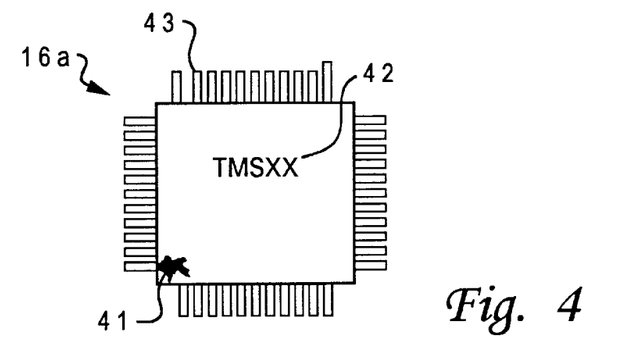
FIG. 4 is a view of a QFP packaged semiconductor device under 2D inspection using the methods of the invention.

Referring now to FIG. 2, ring-light 18 provides light 32 and 33 onto workpiece to be inspected 16 from all sides of camera 17 for the 2D inspection. The reflections 34 and 35 are imaged through lens 15 and received into camera 17, typically a CCD imaging camera. The particular type of light can vary depending on the criteria to be inspected. Some types of criteria are highlighted only by ring-light mounted high, while others can only be illuminated by strobed light mounted low. The image produced by the 2D lighting, of a typical QFP device is shown in FIG. 4. Referring to FIG. 3, a view of the optical path for 3D inspection is shown. In this embodiment, four sources of flat-beam of laser-light are mounted on four linear positioners at right angles to each other. In an alternative arrangement, the four laser sources could sweep to cover the same range covered by the flat beams. Two of the laser sources, 11 and 12, are mounted to linear positioners 13 and 14 respectively. The remaining two laser sources and linear positioners would be perpendicular to the plane of the figure and are not shown. Two perpendicular Linear positioners 13 and 14 can move toward camera 17 in direction 39 for linear positioner 13 and direction 40 for linear positioner 14; they can also move away from the camera in the opposite directions. A laser beam 37 strikes the workpiece to be inspected 16. The reflection has some secondary reflection 38 which goes straight up through lens 15 into camera 17. The triangulation effect is described below with the image of a QFP as seen by the camera as depicted below in FIG. 5.

FIG. 4 shows a top view of a QFP packaged integrated circuit device under 2D lighting designed to highlight voids 41 and package marking 42. This lighting is provided such that after the camera captures the image, the computer system and software can analyze the image data to determine if voids exist in the plastic package and that the quality of marking 42 is acceptable under pre-set criteria. Typically, the software application used in the computer system identifies the marking 42 and compares it to a predefined set of acceptable templates or other measures, and if the package marking falls within a certain acceptable threshold or range, the marking is acceptable. Other defect classification approaches could be used. If the marking is not considered acceptable, the package marking is classified as having a certain defect, and either an indication is immediately made to the operator, or the defect is logged in a form that is available for later use in identifying the defective units. In addition, the camera in conjunction with the computer and software makes it possible to detect and note the X and Y location of the leads, 43. The system uses the X and Y location information to determine the integrity of lead dimensions and identify defects such as bent-lead and lead pitch defects. In addition, the X and Y location of the leads is used to control and strobe the laser light at the right spot for the camera to determine 3 D information in subsequent steps.

Figures 5A, 5B:
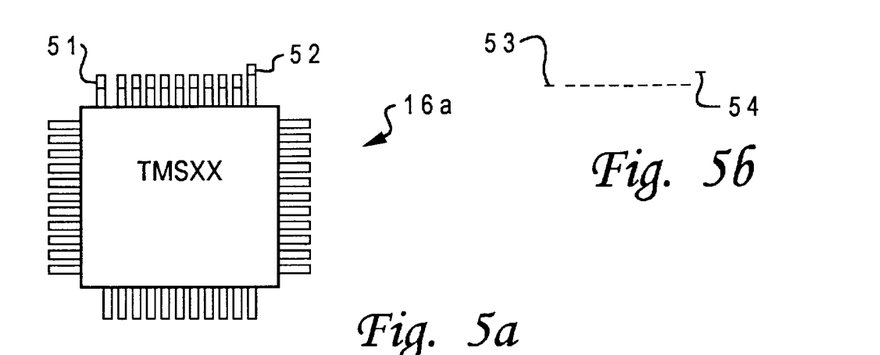
FIG. 5a is a view of an image of a QFP packaged semiconductor device under 3D inspection.
FIG. 5b is the image of the QFP of FIG. 5a as captured by the camera according to the invention.

Referring to FIG. 5, a QFP 16*a* is under 3D lighting designed to highlight dimensional defects such as coplanarity of leads or other normally coplanar surfaces. The laser light reflects back from the leads as shown in 51. A shift 52 in the laser line because the lead being illuminated has lifted by some amount. The camera only detects the view as shown by laser light 53 falling on the leads with the defect being highlighted by 54. The leads could have been anywhere in the image, hence the initial picture captured by 2D is analyzed by the computer and the application software to determine the X-Y location of the leads. The laser sources are then moved across the device and fired at approximately the position where the laser would fall on the leads.

Computer and software analysis made on the location of the laser line with respect to the position of the scanner provides information as to the 3d displacement of that lead. The principal behind the computer analysis is based on structured lighting. i.e: if the laser source is at a certain location, and the light is detected by the camera and software at a certain location, then the point at which the laser light fell on the object being examined is at some determinable location in 3D. If the object was either higher or lower in 3D,(z-axis offset from the X-Y plane) then the laser light would be detected at different locations by the camera. This information can be used to identify defects, or possibly to control lead conditioning equipment which may correct the defect by straightening or otherwise operating on the leads identified as not acceptable by the 3D criteria analysis.

Figures 6A, 6B:
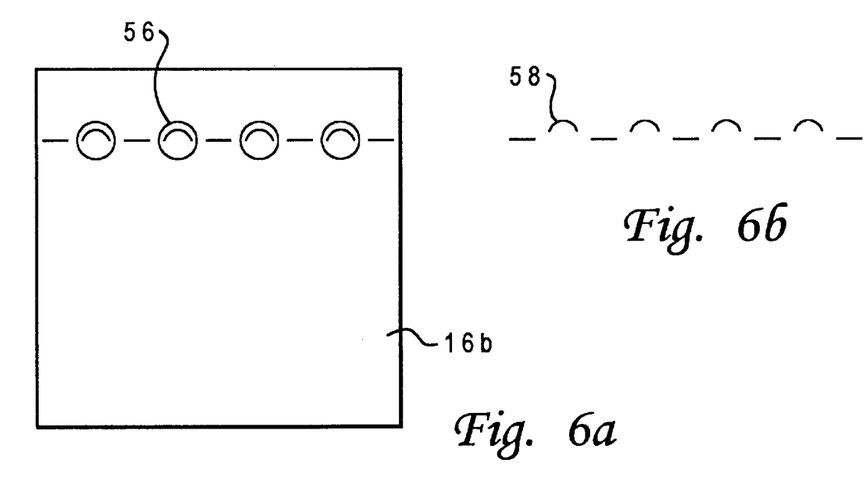
FIG. 6a is a view of an image of a BGA packaged semiconductor device under 3D inspection.
FIG. 6b is the image of the BGA of FIG. 5a as captured by the camera according to the invention.

Referring to FIG. 6, a BGA 16*b* is under 3D lighting designed to highlight dimensional defects such as height, width or location of balls. The laser light reflects back from the balls as shown in 56. A shift would be caused in the laser line if a ball being illuminated was larger or out of location by some amount. The camera only detects the view as shown by laser light 58 reflecting back from the balls. The balls could have been anywhere in the image, hence the initial picture captured by 2D is analyzed by the computer and the application software to determine the X-Y location of the balls. The laser sources are then moved across the device and fired at approximately the position where the laser would fall on the balls. The best reflection is actually before the laser reaches the center of the balls. Computer and software analysis made on the location of the laser line with respect to the position of the scanner provides information as to the 3d displacement of each ball.

Figure 7:
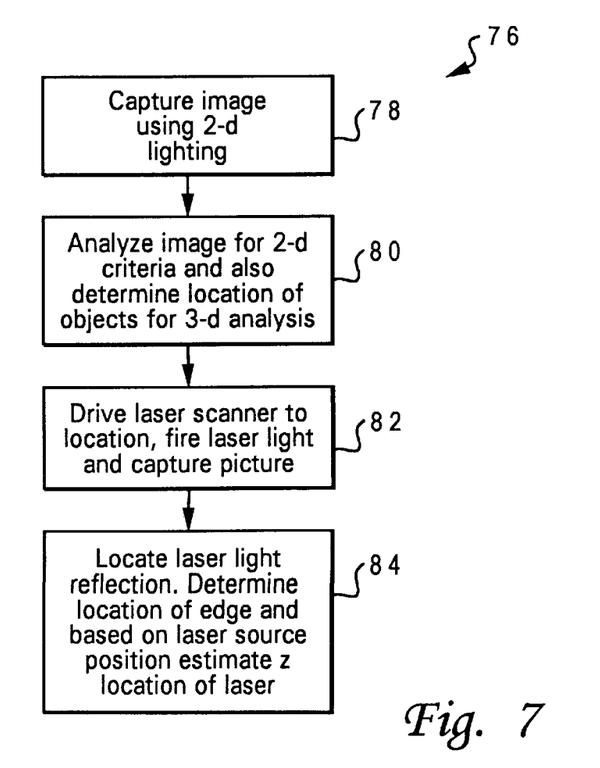
FIG. 7 is a flow diagram representation of a method according to the present invention.

Referring now to FIG. 7, a method for examining a workpiece according to the present invention is referred to generally by reference numeral 76. The first step 78 is performed by illuminating the object and using the CCD camera to capture and store an image.

The second step 80 involves applying software to the captured image data to determine 2D criteria, such as package voids, package marking, and lead locations. This step can complete the 2D analysis and sets up the data required for the 3D analysis. Where the 2D analysis performed by the software indicates a need for further 3D analysis, the third step is performed at those locations.

The third step 82 involves capturing additional image data using the camera and the laser sources at the locations where a 3D criteria inspection is required.

Finally, the data collected in the third step is used to perform the 3D criteria inspection 84. Software techniques are used to determine where the laser reflections are expected to occur from the laser sources fired in the third step. The actual reflection data is compared to the expected data to determine if a z-axis offset (such as bent lead defect or other non-planar defect) has occurred, and if so, an estimate of the offset in the z axis direction can be determined. This information can be reported immediately, stored as a log with respect to the particular device, or used to drive lead conditioning equipment to attempt to correct the defect, or otherwise used by the system. Also, if the estimated z-axis offset is compared to a predetermined threshold or range, the software can indicate whether the offset is within user defined acceptable limits or whether it can be corrected, or not.

Figure 8:
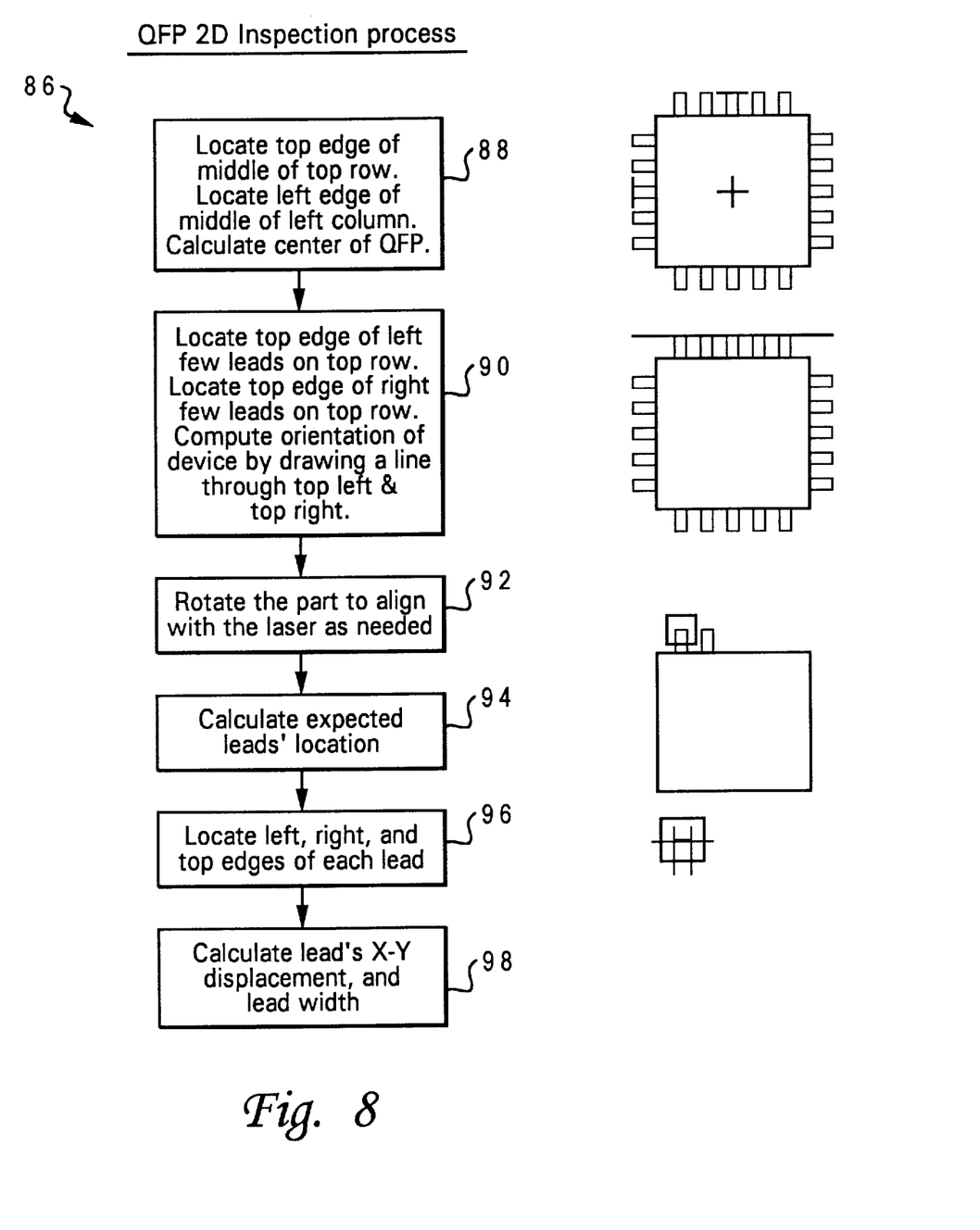
FIG. 8 is a flow diagram representation of a method according to the present invention for 2D inspection of a QFP packaged semiconductor device.
Figure 9:
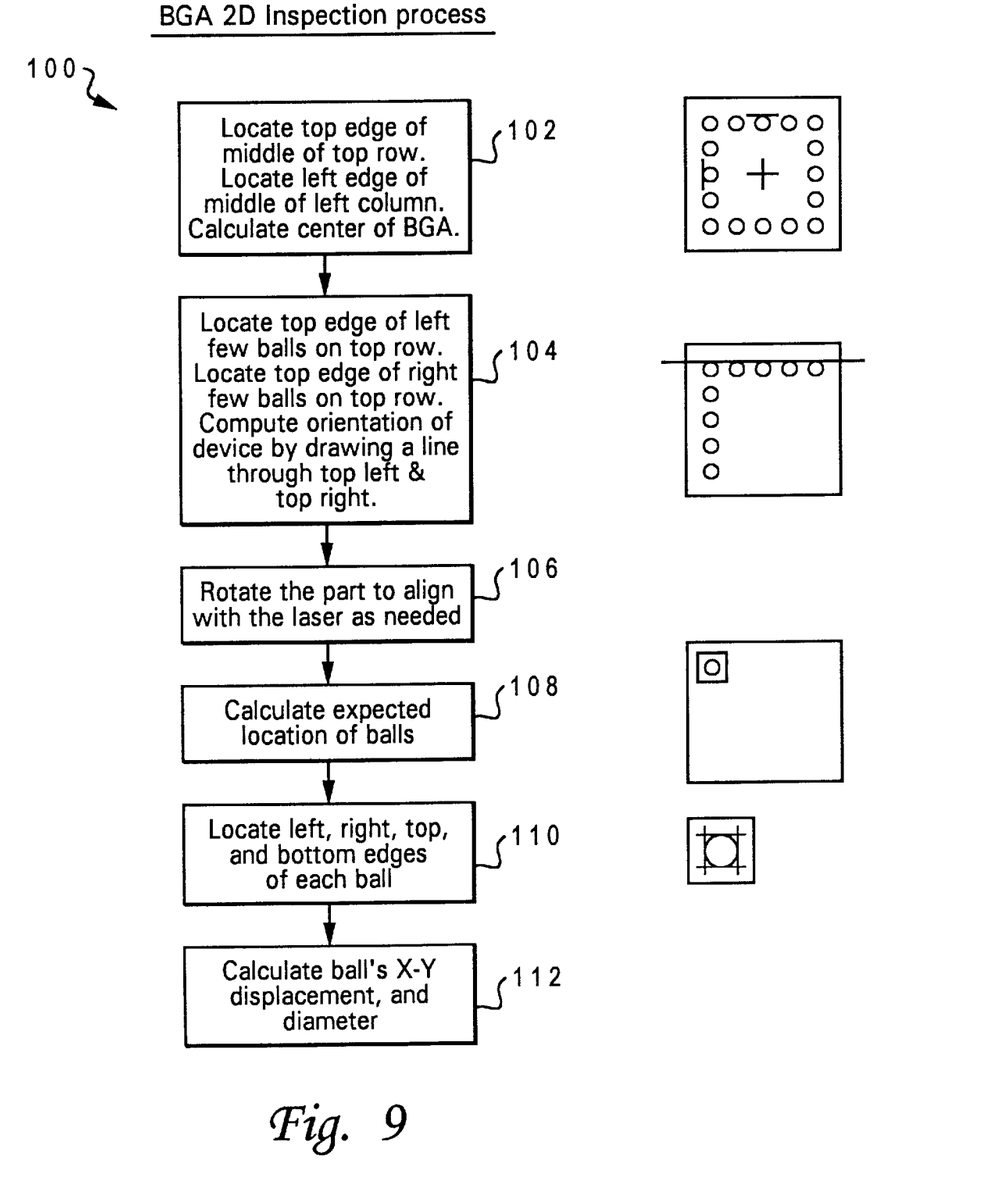
FIG. 9 is a flow diagram representation of a method according to the present invention for 2D inspection of a BGA packaged semiconductor device.
Figure 10:
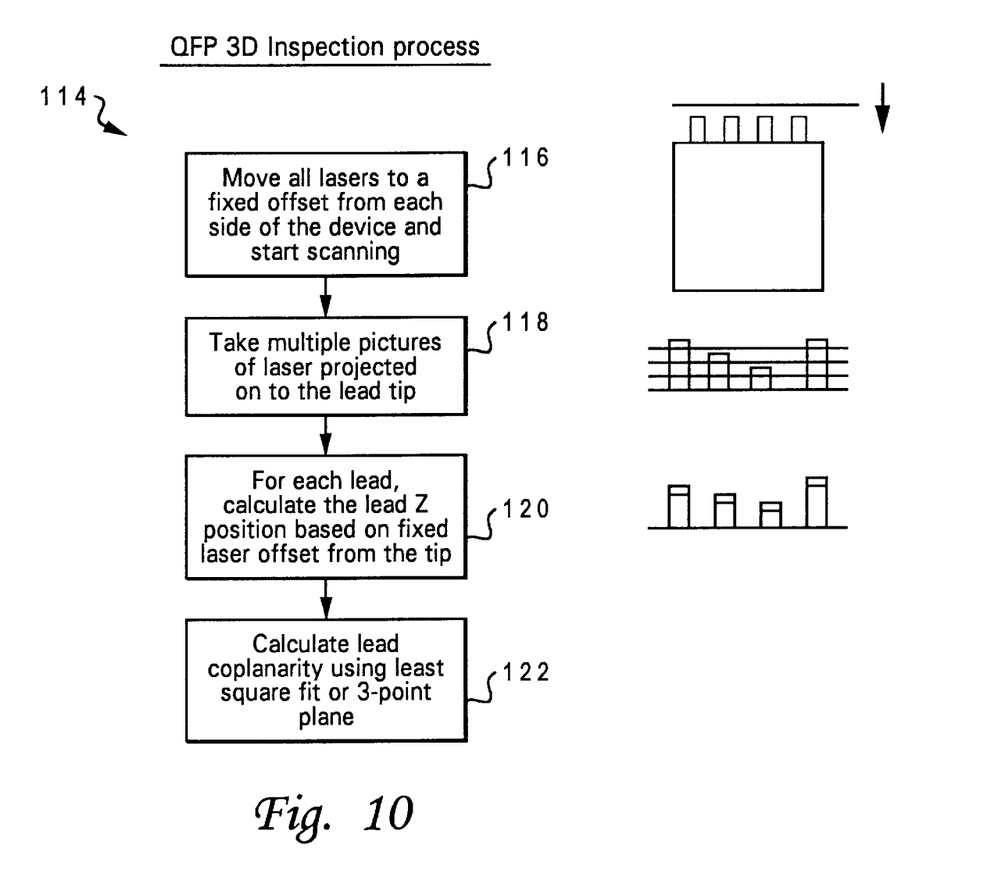
FIG. 10 is a flow diagram representation of a method according to the present invention for 3D inspection of a QFP packaged semiconductor device.

Referring now to FIGS. 8 and 10, a method 100 for 2D inspection of BGA packaged devices or CSP packages is similar to the QFP packaged device inspection method 86. First, locate 88 two edges of the rows of leads which are at right angles to each other for the QFP or locate 102 two edge rows of balls at right angles to each other, in the embodiments as illustrated referred to as a top edge and a left edge and calculate the center of the workpiece. Next, locate 90 the outside edge of a few leads on each side of a row for the QFP or locate 104 the outside edge of a few balls of an outside row for a BGA, in the embodiments illustrated a few leads or a few balls both to the left and right of the top edge to determine the orientation of the workpiece. A step 92 for QFP and 106 for BGA of rotating the workpiece as needed is performed prior to the two dimensional criteria analysis and then the subsequent three dimensional criteria analysis for each ball. Calculate 94 and 108 the expected location of each lead or ball respectively, the actually locate each lead or ball. At this point, any displacement of leads of balls in an x-y, two dimensional, fashion can be calculated 98 and 112 respectively. Again, software in the two dimensional criteria analysis can perform certain inspections and collect location data which is used to drive the three dimensional criteria analysis.

Figure 11:
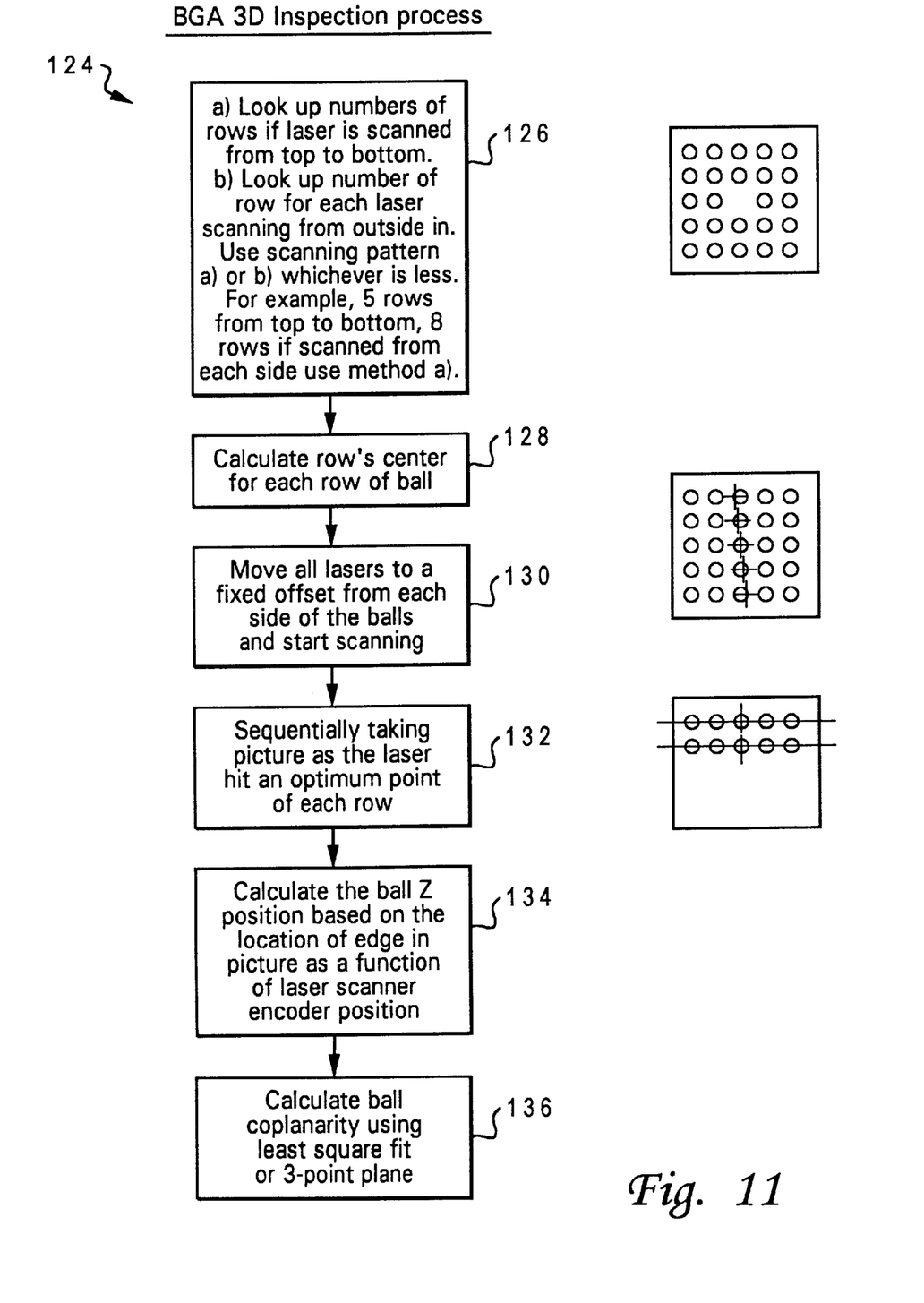
FIG. 11 is a flow diagram representation of a method according to the present invention for 3D inspection of a BGA packaged semiconductor device.

Referring now to FIG. 10 and FIG. 11, after the two dimensional image is collected, the laser head is moved 116 or 130 from the outside of the device towards the inside and at appropriate locations, the laser sources are fired and images collected 118 or 132 by the camera. For BGA packages, the number and location of rows must first be found 126 and the center for each row calculated 128. The positions of the reflections are determined 120 or 134 and the coplanarity is calculated 122 or 136 by software to identify 3D criteria and to locate defects in lead positions or length or ball positions or height, and other defects that are of particular interest in lead semiconductor packages or solder ball bearing semiconductor packages. This step is continued until all the rows of solder balls are inspected on each side of the device, or in the case of an array style BGA package, all the way across the packaged device.

The methods and apparatus described herein can also be extended to the visual inspection of many other devices and in many industries. For example, inspection of balls used in "flip chip" packages or inspection of unpackaged integrated circuit die is contemplated. Automated inspection of completed wire bonds for wire bond loop height and other criteria is also contemplated herein. Inspection of sub assemblies such as those used for disk drives, keyboards, CD-Roms and other such devices are also contemplated. Practitioners skilled in the art will recognize the utility and advantages of this invention in many other applications, all of which are contemplated as part of the invention described herein and as claimed in the appended claims.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

From the foregoing it will be seen that this invention is well adapted to attain all of the ends and objectives hereinabove set forth, together with other advantages which are inherent to the apparatus.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the figures of the accompanying drawings is to be interpreted as illustrative and not in a limiting sense.

What is claimed is:

1. A system for the inspection of a workpiece, the system comprising in combination:

a camera held in a position facing the workpiece;

a ring light positioned to shine on the workpiece from all sides of the camera;

at least one linear positioner which can move toward the camera and away from the camera; and at least one laser mounted on the at least one linear positioner at an angle to the direction faced by the camera, wherein the linear positioner can move to a position wherein the laser is aimed at the workpiece.

2. A system according to claim 1 wherein the at least one linear positioner comprises four linear positioners placed on four different sides of the camera, and the at least one laser comprises four lasers, one laser mounted on each of the four linear positioners.

3. A system according to claim 2 further comprising a computer controlling the camera, the ring light, the linear positioners, and the lasers.

4. A system according to claim 2 wherein the workpiece has a substantially flat rectangular top surface and a substantially flat rectangular bottom surface and four edges connecting the two substantially flat surfaces, with a row of electrical leads extending from each of the four edges, and wherein the camera faces one of the substantially flat rectangular surfaces, and the four linear positioners approach the camera from directions which are perpendicular to the four edges of the workpiece and can move to positions wherein the lasers are aimed at the rows of electrical leads.

5. A system according to claim 4 wherein each laser projects a flat beam directly across a row of electrical leads.

6. A system according to claim 4 wherein each laser sweeps a beam directly across a row of electrical leads.

7. A system according to claim 3 wherein the workpiece has a substantially flat rectangular top surface and a substantially flat rectangular bottom surface and four edges connecting the two substantially flat surfaces, with a row of electrical leads extending from each of the four edges, and wherein the camera faces one of the substantially flat rectangular surfaces, and the four linear positioners approach the camera from directions which are perpendicular to the four edges of the workpiece and can move to positions wherein the lasers are aimed at the rows of electrical leads.

8. A system according to claim 3 wherein the workpiece has at least one substantially flat surface and a ball grid array on the at least one substantially flat surface, and wherein the camera faces the at least one substantially flat surface, and the four linear positioners approach the camera from directions which are perpendicular to the ball grid array and can move to positions wherein the lasers are aimed at the rows and columns of the ball grid array.

9. A system according to claim 8 wherein each laser projects a flat beam directly across a row or column of the ball grid array.

10. A system according to claim 8 wherein each laser sweeps a beam directly across a row or column of the ball grid array.

11. A system according to claim 1 further comprising a computer operably connected to and controlling the camera, the ring light, the at least one linear positioner, and the at least one laser.

12. A system according to claim 11 wherein the workpiece has a substantially flat surface and a substantially linear edge with a row of electrical leads extending from the edge, and wherein the camera faces the substantially flat surface, and the at least one linear positioner approaches the camera from a direction which is perpendicular to the edge of the workpiece and can move to a position wherein the at least one laser is aimed at the row of electrical leads.

13. A system according to claim 12 wherein the at least one laser projects a flat beam directly across the row of electrical leads.

14. A system according to claim 12 wherein the at least one laser sweeps a beam directly across the row of electrical leads.

15. A system according to claim 11 wherein the workpiece has at least one substantially flat surface and a ball grid array on the at least one substantially flat surface, and wherein the camera faces the at least one substantially flat surface, and the at least one linear positioner approaches the camera from a direction which is perpendicular to the rows or columns of the ball grid array and can move to positions wherein the at least one laser is aimed at the rows or the columns of the array.

16. A system according to claim 15 wherein the at least one laser projects a flat beam directly across a row or column of the ball grid array.

17. A system according to claim 15 wherein the at least one laser sweeps a beam directly across a row or column of the ball grid array.

* * * * *